United States Patent [19]

Macnamee

[11] Patent Number: 5,760,024
[45] Date of Patent: Jun. 2, 1998

[54] METHOD OF USING ASPIRIN TO IMPLANT AN EMBRYO

[75] Inventor: Michael Macnamee, Cambridge, United Kingdom

[73] Assignee: Applied Research Systems ARS Holding N.V., Curacao, Netherlands

[21] Appl. No.: 464,785

[22] PCT Filed: Dec. 24, 1993

[86] PCT No.: PCT/GB93/02657

§ 371 Date: Jun. 23, 1995

§ 102(e) Date: Jun. 23, 1995

[87] PCT Pub. No.: WO94/15613

PCT Pub. Date: Jul. 21, 1995

[30] Foreign Application Priority Data

Dec. 30, 1992 [GB] United Kingdom ............... 9227123

[51] Int. Cl.$^6$ .................................................. A61K 31/60
[52] U.S. Cl. ........................................................ 514/165
[58] Field of Search ............................................ 514/165

[56] References Cited

FOREIGN PATENT DOCUMENTS

| 91014 | 2/1987 | Romania . |
| 90/13299 | 11/1990 | WIPO . |

OTHER PUBLICATIONS

Kautiainen M., et al., "Effects of Drugs on Perfusion and Intrauterine Pressure in Isolated Human Uterus", Database Embase, Elsevier Science Publishers, Amsterdam, NL. (1979).

Takashima, M., et al., "A Trial of Low–Dose Aspirin Therapy in High–Risk Pregnancy", Database Medline, U.S. National Library of Medicine (NLM), Bethesda, MD. (abstract), 1980.

Zeev Weiner, et al., "Umbilical and Uterine Artery Flow Velocity Waveforms in Pregnant Women With Systemic Lupus Erthematosus Treated With Aspirin and Glucocorticosteroids", Am. J. Repr. Immunol., vol. 28, No. 3–4, 1992, pp. 168–171.

C.M.G. Thomas, et al., "Effect of Prostaglandin F2 Alpha, Indomethacin and Estradiol on Ovum Transport and Pregnancy in the Golden Hamster", Biology of Reproduction, vol. 23, 1980, pp. 687–698.

R.K. Goswamy, et al., "Decreased Uterine Prefusion—A Cause of Infertility", Human Reproduction, vol. 3, No. 8, 1988, pp. 955–959.

K. Wollenhaupt, et al., "Untersuchungen zur Beeinflussung des Implantationsgeschehens bei Ratten und Sauen durch perorale Verabreichung von Prostaglandinsynthetasehemmern", Arch. Exper. Vet. Med., vol. 35, No. 3, 1981, pp. 465–470.

*Primary Examiner*—Marianne M. Cintins
*Assistant Examiner*—M. Moezie
*Attorney, Agent, or Firm*—Ostrolenk, Faber, Gerb & Soffen, LLP

[57] ABSTRACT

The invention provides the use of a cyclooxygenase inhibitor such as the non-steroidal anti-inflammatory agent aspirin in the manufacture of a medicament to enhance perfusion of blood through the mammalian, preferably human, uterus. The enhanced perfusion aids embryo implantation in natural or assisted methods of conception.

7 Claims, No Drawings

1

METHOD OF USING ASPIRIN TO IMPLANT AN EMBRYO

This application is a 371 of PCT/GB93/02657 filed Dec. 24, 1993.

The present invention is concerned with human conception and embryo development, in particular embryo implantation into the uterine endometrium.

In humans, the inability to conceive often causes considerable distress and frequently adults with fertility problems undergo protracted and expensive courses of treatment in an effort to achieve a successful pregnancy. Unfortunately, the failure rate of such treatment remains high.

Research into the causes of infertility has shown several contributing factors, each or any of which could be responsible for the problem experienced by a particular patient. Thus, poor gamete quality, congenital anatomical abnormalities and/or surgical complications can all result in infertility.

Some causes of infertility have been treated with ovarian stimulants to regulate follicle growth, oocyte maturation and ovulation. For example, the gonadotrophins HMG (human menopausal gonadotrophin) and HCG (human chorionic gonadotrophin) have been used to induce superovulatory responses in amenorrhoeic women and stimulated menstrual cycles have been induced using clomiphene or HMG.

Following the development of methodologies suitable for in vitro fertilisation and in vitro growth of the fertilised oocyte up to the blastocyst stage, in vitro fertilisation (IVF) has become a popular, and reasonably successful, means of achieving pregnancy. In IVF gametes are collected from each of the parents, optionally after hormonal treatments to induce gamete production. The collected oocytes are then matured and fertilised in vitro. The resulting pronucleate eggs are transferred to a richer culture medium and grown for up to 4 or 5 days to form a blastocyst. Up to three embryos usually developed to the early cleavage stages may be selected for replacement into the uterus which has either been prepared for implantation naturally or by hormonal treatments.

Cryopreservation of pronucleate eggs, early cleavage stage embryos and blastocysts is now possible allowing more flexibility both in the treatment regime and also in research.

However, the improvements in embryological techniques since the 1980s-has failed to significantly increase the proportion of pregnancies achieved by patients treated. Successful implantation requires not only the correct development of the embryo and the preparation of a receptive endometrium within the uterus, but also the successful attachment of the embryo to the uterine epithelial surface with decidualisation of the endometrium and maintenance of the corpus luteum. Despite the transfer of multiple embryos fertilised in vitro, 90% of these embryos do not thrive and the overall chance of an embryo implanting remains at a mere 15%. Generally up to 3 embryos are replaced (ie. introduced into the uterus) to improve the prospects of implantation but pregnancy still only occurs in 20-30% of all patients.

Implantation involves a complex series of events involving both the embryo and uterus, and is deemed to have taken place when the embryo is physically established at a fixed position within the uterus and, in humans, when trophoblastic invasion of the endometrial lining has occurred. The hormonal events required for implantation are involved and remain poorly understood (see Bonney et al in Baillieres Clinical Endocrinology and Metabolism 4:207-231 (1990) and Smith in Baillieres Clinical Obstetrics and Gynaecology 5:73-93 (1991)) and it is now generally accepted that an improvement in implantation rates would significantly enhance the success of in vitro fertilisation and embryo transfer.

One explanation given for the failure of implantation by embryos and thus infertility is poor uterine perfusion (see Goswamy et al. Human Reproduction 3, No.8 pages 955-959 (1988)). Several different stimuli have been shown to cause an increase in endometrial vascular permeability and decidualisation and in each case the mechanism involved appears to be associated with the synthesis and/or release of prostaglandins (see Bonney et al. supra).

In animal models prostaglandins have been shown to assist embryo implantation by increasing vascular permeability, inducing a mild inflammatory reaction, eedema and decidualisation. Inhibitors of prostaglandin synthesis such as aspirin, prevent embryo implantation in the mouse and rat (see Kennedy in Eicosanoids and. Reproduction, MTP Press (ed Hillier), page 73) and it has been postulated that a similar effect could occur in humans (see Smith, supra).

However, it has now been found that low doses of non-steroidal anti-inflammatory agents (which are in general cyclooxygenase inhibitors) improve endometrial arteriolar perfusion and enhance embryo implantation rates. Non-steroidal anti-inflammatory agents include aspirin (2-acetoxybenzoic acid and/or salts thereof), ibuprofen, indomethacin, naproxen. Other agents are given in Martindale The Extra Pharmacopoeia 29th edition (published by the Pharmaceutical Press).

The present invention thus provides the use of cyclooxygenase inhibitors, for example aspirin (2-acetoxybenzoic acid or salts thereof), in the manufacture of a medicament to enhance perfusion of blood through the mammalian, for example human, uterus.

Furthermore, the present invention also provides the use of cyclooxygenase inhibitors, for example aspirin (2-acetoxybenzoic acid or salts thereof), in the manufacture of a medicament to enhance embryo implantation in the mammalian, for example human, uterus.

The enhanced uterine perfusion prepares the endometrium for embryo implantation and so promotes the likelihood of implantation of the embryo. Embryo implantation is assisted whether fertilisation occurs in vivo (including natural fertilisation events) or in vitro. In particular, the present invention is suitable for use with all forms of assisted conception including IVF, GIFT (gamete intrafallopian transfer), DIPI (direct intraperitoneal insemination of sperm), IUI (intrauterine insemination) and methods involving hormone replacement therapy (HRT).

We have found that the use of low doses of the agents according to the invention can be used prophylactically in females who have a history of poor uterine perfusion for example by administration at the commencement of hormone replacement therapy treatment. Thus viewed from another aspect, the present invention provides the use of cycloxygenase inhibitors, for example aspirin (2-acetoxybenzoic acid or salts thereof), in the manufacture of a medicament for the prophylaxis of impaired perfusion of blood through the mammalian, preferably human, uterus.

Whilst we do not wish to be bound by the theoretical considerations, we believe the effect of aspirin in increasing uterine blood perfusion is caused by an alteration of the balance between thromboxane and prostacyclin. Thromboxane is a powerful vasoconstrictor and enhances platelet aggregation, whilst prostacyclin is a strong vasodilator and an inhibitor of platelet aggregation. Aspirin is an inhibitor of cycloxygenase, and so inhibits the synthesis of both prostacyclin and thromboxane. The other non-steroidal anti-inflammatory agents are believed to act in a similar manner.

According to the present invention, low doses of non-steroidal anti-inflammatory agents should be administered at regular intervals for a short period eg. 2 to 20 days (for example 2 to 7 days) prior to implantation. Administration may be continued up to and following confirmation of pregnancy for up to 11 weeks after implantation.

Generally a dosage of from 50 to 500 mg, generally 75 to 300 mg and preferably 100 to 200 mg, of non-steroidal anti-inflammatory agent should be taken every one or two days. The agent may be administered in any convenient form and by any suitable means. For example, aspirin may be administered as a solution, by injection or as a tablet, capsule or liquid for oral administration. Transdermal or subcutaneous patches or implants can also be used to provide the agent. Generally, oral administration in any form is the most convenient and this method is preferred.

Where desired, the patient may also receive hormonal treatment including buserelin or other LHRH agonists, oestradiol, oestrogen, progesterone, gonadorelin, menotrophin or any other hormone, hormonal analogue, agonist or antagonist.

In one embodiment, the present invention provides a composition comprising a cycloxygenase inhibitor such as aspirin in combination with at least one hormone which affects conception. Such a product may also be provided as a combined preparation in a form suitable for simultaneous, separate or sequential use.

Successful embryo implantation can be detected by any conventional means, but is conveniently detected by ultrasound scanning.

Uterine blood flow and thus any improvement in uterine perfusion can be measured by transvaginal colour flow imaging or Doppler ultrasound of the uterine arteries, or by any other suitable technique.

The present invention also provides a method of enhancing blood perfusion in a uterus of a mammal, for example a human, said method comprising administration of a cycloxygenase inhibitor, for example aspirin, to said mammal.

Further, the present invention provides a method of implanting an embryo into the uterine endometrium of a mammal, for example a human, said method comprising administrating a cycloxygenase inhibitor, for example aspirin, to said mammal prior to implantation.

The invention is further illustrated by the following Examples:

EXAMPLE 1

Between April 1991 and March 1992, 213 frozen/thawed embryo transfer cycles were carried out at Bourn Hall Clinic, Cambridge, UK. Of these, 103 were in natural menstrual cycles and 110 in hormone replacement therapy (HRT) cycles, which were initiated after induction of a hypogonatrophic state using the LHRH agonist buserelin (Superfact, Hoechst, U.K). The protocols for pituitary desensitization, administration of oestradiol and progesterone and timing of embryo transfer in both HRT and natural cycles are as described by Sathanandan et al. in Human Reproduction 6:685–687 (1991).

Uterine blood flow was measured by transvaginal colour flow imaging (Sonotron, Diasonic Sonotron Ltd, UK) of the uterine arteries on day 13 of HRT cycles in 70 patients. Flow velocity wave forms and blood flow impedance were recorded and the pulsatility index measured. Good uterine perfusion was recorded in 56 patients (80%). In the remainder, aspirin (150 mg B.D.) was given orally and the dose of oestradiol in the HRT cycle was maintained. Repeat measurements of uterine perfusion were made 2–3 days later. Improved uterine perfusion was recorded in 12 of these patients (86%) and embryo transfer was performed. The remaining two cycles were abandoned due to persistently poor uterine perfusion. Clinical pregnancies were confirmed by the detection of a gestational sac by ultrasound scanning 33–35 days after embryo transfer. In treated patients, aspirin was continued until 11 weeks of pregnancy.

Table 1 shows the clinical pregnancy and implantation rates per embryo transferred. There is no difference in patient's age, duration of infertility, number of embryos replaced and quality of embryos, between the natural cycle, HRT alone and HRT with aspirin patient groups. The pregnancy and implantation rates between natural and HRT cycles are not different. The highest implantation and clinical pregnancy rates are seen in the group treated with aspirin and HRT, however there is no significant difference between the two groups.

TABLE 1

PREGNANCY AND IMPLANTATION RATES BY CYCLE TYPE

| Type of cycle | Number of embryo transfer cycles | Clinical pregnancies (rate) | Implantation per embryo transfer |
|---|---|---|---|
| NATURAL | 103 | 25(24%) | 25/254(10%) |
| HRT | 98 | 23(23%) | 25/257(10%) |
| HRT PLUS ASPIRIN | 12 | 6(50%) | 8/33 (24%) |

EXAMPLE 2

Methods

A total of 176 frozen embryo replacement (FER) cycles were undertaken by 99 women between 1991 and 1993 using artificial cycles. Uterine blood flow was measured in all cycles by a transvaginal colour Doppler ultrasound. All women had previously received ovarian stimulation using follicle stimulating hormone (FSH; Metrodin, Serono Laboratories, Welwyn Garden City, UK) and/or human menopausal gonadotrophin (HMG; Pergonal, Serono Laboratories, Welwyn Garden City, UK) combined with luteinising hormone-releasing hormone (LHRH) agonist (Macnamee & Brinsden, 1992, in 'A Textbook of in vitro Fertilisation ed. Brinsden, P. R. and Rainsbury P. A., Parthenon Publishing Group, UK).

1. Buserelin/HRT protocol

Buserelin 500 mcg subcutaneous daily was started on day 22 of menses to achieve pituitary desensitisation. Endometrial development was promoted using a hormone replacement therapy (HRT) protocol. The regime was oestradiol valerate (Progynova; Schering, UK) 2 mg orally daily from days 1–5, 2 mg twice daily from days 6–9 and 2 mg three times daily from day 10 onwards and injections of progesterone (Gestone, Payne & Burn Ltd, UK) 50 mg daily for 2 days and 100 mg daily thereafter (Sathanandan et al, 1991 Supra). The initial dose of gestone was given between the 15th and 21st day of HRT when satisfactory uterine perfusion had been achieved. The cycle was abandoned in those who had not achieved good uterine perfusion by day 21 of HRT. The embryo transfer was scheduled for the third day of progesterone injections in those who continued the FER cycle. Women becoming pregnant continued the HRT until the 12th week of gestation.

2. Assessment of uterine perfusion

The initial assessment of uterine perfusion was on the 13th day of HRT. A phillips/Vingmed CFM 7000 Doppler ultrasound system with a trans-vaginal probe was used. The blood flow velocity waveform (FVW) of the anterior branch of the right and left uterine arteries were measured and classified according to the following criteria: (i) type "O", when there was no diastolic forward flow, (ii) type "A" the diastolic flow was present but not continuous with the preceding systolic waveform, (iii) type "B", the diastolic flow was continuous with the preceding systolic waveform but not extending to the next cardiac cycle and (iv) type "C", the diastolic and systolic waveforms were continuous from one cycle to the next (Goswamy et al, 1988 Hum. Reprod. 3, 955–959). The pulsatility index (PI) was defined as the peak-to-peak excursion of the waveforms divided by the mean height (Steer et al, 1992, Fertil. Steril. 57, 372–376). The results were classified as PI less than or greater than 3. When poor uterine perfusion was observed (i.e. FVW type O or A and PI>3), the Doppler examinations were repeated every two days until an improvement was seen or until the cycle was abandoned.

3. Aspirin administration

Initial FER cycles

Women with poor uterine perfusion at the first Doppler ultrasound examination in their initial attempts (group I, n=37) received low-dose aspirin (150 mg once daily) from the 13th day of HRT onwards.

Subsequent FER cycles

Women from group I (n=23) received aspirin electively from day 1 of subsequent HRT, but 10 did not. The latter 10 women again began aspirin on day 13 of the subsequent HRT when poor uterine perfusion was again observed. Those receiving or not receiving aspirin in each group were not randomised. Women on aspirin therapy continued the treatment until the demonstration of fetal heart activity if they achieved a pregnancy.

4. Statistical analysis

Proportions were compared using Fisher's Exact Probability tests. Means were compared using the two-tailed Mann-Withney-U tests. Differences were considered significant if $p<0.05$.

Results

There were no differences between those women who did or did not start aspirin therapy on day 1 of their subsequent HRT cycles in terms of age, cause of infertility and ovarian response to induction of ovulation in the cycles from which embryos in the present study were generated.

In group I, 57% of those who received aspirin from the 13th day of HRT in their initial cycles achieved good uterine blood flow and reached embryo transfer compared with 83% ($p<0.05$) and 60% respectively of those who did or did not start aspirin on the 1st day of subsequent HRT (Table II).

TABLE II

Results of the initial and subsequent frozen embryo replacement in group I

|  | Initial cycles | Subsequent cycles | |
| --- | --- | --- | --- |
| Day aspirin started* | 13 | 1 | 13 |
| No. women | 37 | 23 | 10 |
| No. cancelled | 16(43%)a | 4(17%)b | 4(40%) |
| No. reaching embryo transfer | 21(57%)a | 19(83%)b | 6(60%) |
| Clinical pregnancy rate per embryo transfer | 4(19%) | 9(47%) | 1(17%) |

*day of hormone replacement therapy (HRT) aspirin was started
HRT = hormone replacement therapy
a versus b: $p < 0.05$ The clinical pregnancy rate per embryo transfer was 19% in the initial cycles when aspirin was started on the 13th day of HRT (Table II). The pregnancy rates were 43% and 17% respectively in the subsequent cycles for the women who did or did not receive aspirin electively from the first day of HRT. The differences did not reach statistical significance.

These results indicate that low-dose aspirin may be effectively used without adverse effect on the process of embryo implantation, both prophylactically ie. prior to the HRT treatment, in preventing impaired uterine perfusion, and also therapeutically in improving established conditions of impaired uterine flow.

What is claimed is:

1. In a method of implanting an embryo into the uterine endometrium of a healthy mammal the improvement which comprises administering aspirin to said mammal prior to implantation.

2. The method of claim 1 in which the aspirin is administered in an amount of 50–500 mg every one to two days.

3. The method of claim 2 wherein the said amount is 75–300 mg.

4. The method of claim 3 wherein said amount is 100–200 mg.

5. The method of claim 1 wherein said aspirin administration is commenced 2 to 20 days prior to implantation.

6. The method of claim 5 wherein said administration is continued for up to 11 weeks after implantation.

7. The method of claim 1 in which the method improved by the said administration is in vitro fertilization.

* * * * *